United States Patent
Chen

(10) Patent No.: US 10,792,197 B2
(45) Date of Patent: Oct. 6, 2020

(54) SURGICAL SPONGE

(71) Applicant: Multigate Medical Products Pty, Ltd, Homebush West, NSW (AU)

(72) Inventor: Ben Chen, Cecil Park (AU)

(73) Assignee: Multigate Medical Products Pty Ltd, Homebush West, NSW (AU)

( * ) Notice: Subject to any disclaimer, the term of this patent is extended or adjusted under 35 U.S.C. 154(b) by 228 days.

(21) Appl. No.: 14/933,463

(22) Filed: Nov. 5, 2015

(65) Prior Publication Data

US 2016/0367409 A1 Dec. 22, 2016

(30) Foreign Application Priority Data

Oct. 13, 2014 (AU) ................ 2014904073

(51) Int. Cl.
*A61F 13/44* (2006.01)
*A61B 90/00* (2016.01)
*A61F 13/36* (2006.01)
*A61F 13/84* (2006.01)
*A61F 13/42* (2006.01)

(52) U.S. Cl.
CPC .............. *A61F 13/44* (2013.01); *A61F 13/36* (2013.01); *A61F 13/84* (2013.01); *A61B 2090/3937* (2016.02); *A61F 2013/422* (2013.01)

(58) Field of Classification Search
CPC .. A61B 2090/3937; A61F 13/36; A61F 13/44; A61F 13/84
See application file for complete search history.

(56) References Cited

U.S. PATENT DOCUMENTS

| | | | | |
|---|---|---|---|---|
| 3,867,935 A | * | 2/1975 | Eisdorfer | A61F 13/00034 604/385.201 |
| 3,911,922 A | * | 10/1975 | Kliger | A61F 13/44 428/159 |
| 3,941,132 A | * | 3/1976 | Lenaghan | A61F 13/44 604/362 |
| 4,068,666 A | * | 1/1978 | Shiff | A61F 13/44 604/362 |
| 4,205,680 A | * | 6/1980 | Marshall | A61F 13/44 604/362 |
| 4,244,369 A | * | 1/1981 | McAvinn | A61F 13/44 604/362 |
| 4,490,146 A | * | 12/1984 | Sergeant | A61F 13/36 604/358 |
| 4,626,251 A | * | 12/1986 | Shen | A61F 13/44 604/362 |
| 4,938,901 A | * | 7/1990 | Groitzsch | A61F 13/44 264/101 |
| 5,575,781 A | * | 11/1996 | DeBusk | A61F 13/44 156/204 |
| 2005/0049563 A1 | * | 3/2005 | Fabian | A61F 13/44 604/362 |

(Continued)

FOREIGN PATENT DOCUMENTS

GB 1539633 A 1/1979
WO WO2015075078 A1 5/2015

*Primary Examiner* — Susan S Su
(74) *Attorney, Agent, or Firm* — Alston & Bird LLP

(57) ABSTRACT

The invention relates to a surgical sponge which includes multiple plies of gauze and stitches. The multiple plies of gauze has one or more open sides. The stitches are adapted to fasten or close the open sides. The stitches are made with one or more contrasting threads.

12 Claims, 8 Drawing Sheets

(56) References Cited

U.S. PATENT DOCUMENTS

| | | | | |
|---|---|---|---|---|
| 2007/0123827 A1* | 5/2007 | Falls, Jr. | ............... | A61F 13/44 |
| | | | | 604/167.01 |
| 2011/0066124 A1* | 3/2011 | Shao | ............... | A61F 13/00008 |
| | | | | 604/358 |
| 2012/0259302 A1* | 10/2012 | Chaisumdet | ............ | A61F 13/36 |
| | | | | 604/367 |
| 2013/0035655 A1* | 2/2013 | Nakamura | ............. | A61F 13/36 |
| | | | | 604/360 |
| 2014/0243770 A1* | 8/2014 | Stewart | ................. | A61F 13/44 |
| | | | | 604/362 |
| 2014/0303606 A1* | 10/2014 | Garner-Richards | ... | A61B 19/44 |
| | | | | 606/1 |

* cited by examiner

SURGICAL SPONGE

RELATED APPLICATION

This application claims priority to Australian Provisional Application No. 2014904073 filed 13 Oct. 2014, which is incorporated herein by reference.

TECHNICAL FIELD

The present invention relates to a surgical sponge. More particularly, the present invention relates to a surgical sponge with contrasting stitching.

BACKGROUND OF THE INVENTION

Gauze sponges are typically used in surgery for absorbing blood and tissue fluids, blunting dissect tissues and protecting important structures during surgical procedures. Gauze sponges for medical use normally include cotton and/or non-woven materials and are provided in many sizes, plies, and fabrics. These sponges are generally soft, low linting and contain a radiopaque strip or thread so that they can be detected and located by X-ray if accidentally left within a wound or inside a patient's body.

There are different types of surgical sponges having different specialties. Abdominal sponges are specifically designed to be used on procedures requiring large incisions, such as laparotomy or thoracotomy. They are also typically moistened with saline and used as pads to protect retracted viscera. Conventionally, abdominal sponges are made up of multiple layers of combination of woven gauze and/or non-woven materials which are sewn together by threads. The thread and gauze are traditionally in matching colour, being white. As such, the stitching would just blend invisibly into the fabric of the gauze. Such a sponge has at least the following shortcomings:
1) the entire sponge becomes less visible when in use during operation, particularly when it is soaked in red blood and body fluids; and
2) it is difficult to identify any loose threads both in the quality control process and during operation.

It is an object of the present invention to provide a sponge which may overcome or ameliorate the above shortcomings, or which will at least provide a useful alternative.

SUMMARY OF THE INVENTION

According to the present invention, there is provided a surgical sponge including: multiple plies of gauze having one or more open sides; and stitches adapted to fasten or close the open sides; wherein the stitches are made with one or more contrasting threads.

Preferably, the threads are in contrast to the gauze in terms of their appearance. Appearance may include colour and/or texture. The texture may include physical composition and structure.

In a preferred embodiment, the gauze is white in colour. The one or more contrasting threads are preferred to be selected from one or a combination of the following: fluoro-lime, fluoro-green or fluoro-yellow. As such, the contrasting thread is readily visible against a white background without being too glaring or striking.

Preferably, the threads are made out of one or more non-absorbing materials. As such, the threads are not susceptible to being stained by blood or other fluids thereby being capable of maintaining their inherent appearance and visibility when in use.

Preferably, the sponge may be five-ply or six-ply. The five-ply sponge may include a sheet of cotton gauze folded in half to form top and bottom plies and three intermediate plies made out of non-woven viscose and/or polyester. The six-ply sponge may include six plies of cotton gauze.

Optionally, the sponge may be partially formed by a sheet of cotton gauze being divided into three equal portions which are folded onto one another.

In a preferred embodiment, each ply is preferred to be rectangular or square in shape. The plies of the sponge are preferred to be sewn together by the one or more threads creating stitches along and around the open sides. More preferably, further stitches are provided diagonally across the surface of the sponge.

BRIEF DESCRIPTION OF THE DRAWINGS

The invention may be better understood from the following non-limiting description of preferred embodiments, in which.

DETAILED DESCRIPTION OF THE DRAWINGS

It should be noted that the threads referred to in this specification are in contrast to the gauze in terms of their general appearance. It will be appreciated that appearance may include colour and/or texture.

Figure 1:
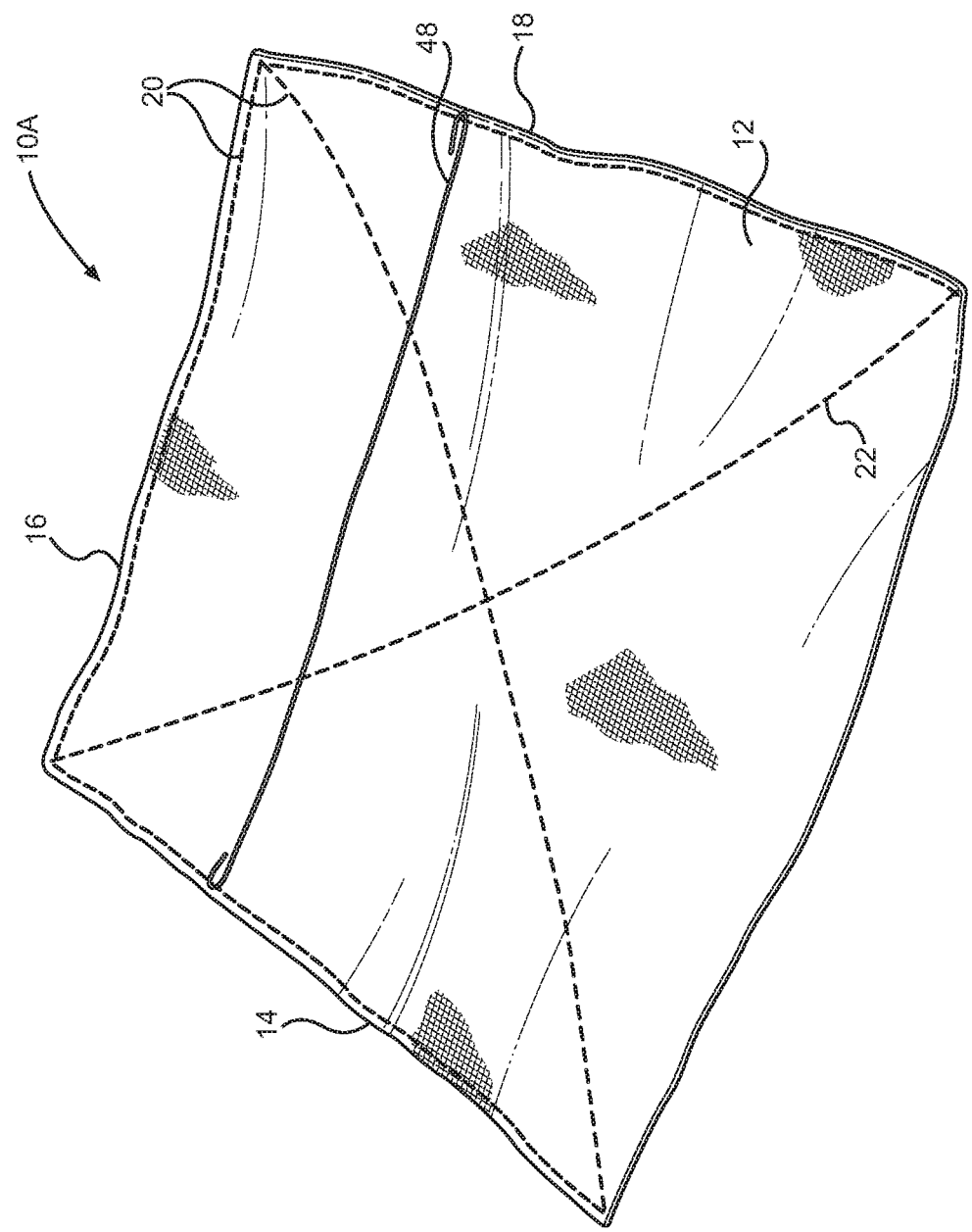
FIG. 1 is a perspective view from above of a surgical sponge in accordance with one preferred embodiment of the present invention.
Figure 2:
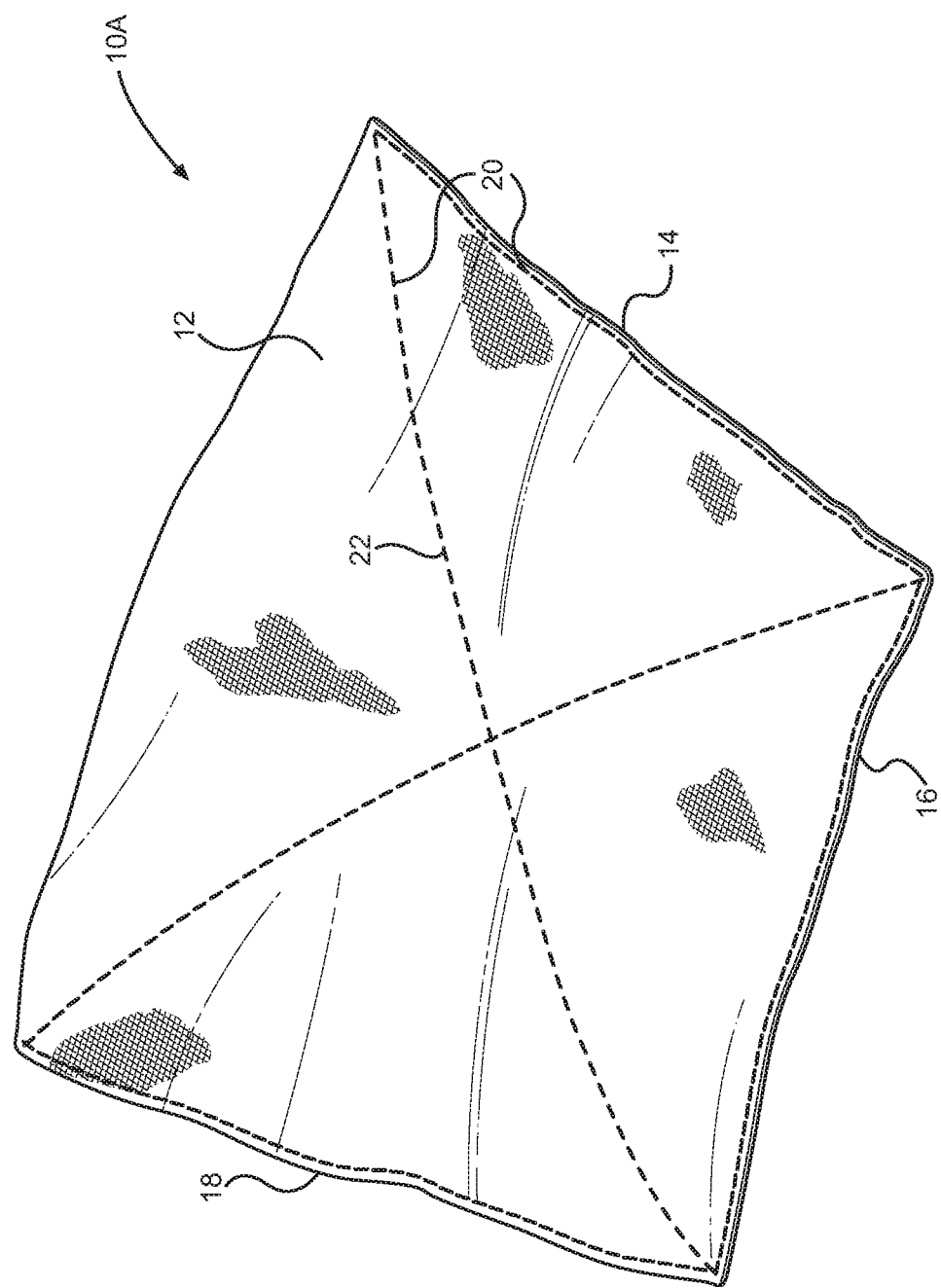
FIG. 2 is a perspective view from below of the surgical sponge of FIG. 1.

Referring to FIGS. 1 to 2, an abdominal sponge 10A is shown having multiple plies of gauze 12. The abdominal sponge 10A has three open sides 14, 16 & 18 and stitches 20 adapted to fasten or close each of the three open sides 14, 16 & 18. The stitches 20 are made with contrasting threads 22.

Although not noticeable from the accompanying drawings which are in black and white, the gauze 22 is substantially white in colour in this embodiment. The contrasting colour of the threads 22 is fluoro-lime in colour in this embodiment. It should however be noted that the colour of the contrasting threads 22 may be selected from one or a combination of the following: fluoro-lime, fluoro-green or fluoro-yellow. These three colours have the commonality that these are relatively subdued fluoro colours. These fluoro colours offer the following benefits:
1) rendering the contrasting threads 22 readily visible yet low key against the white gauze 12 background; and
2) the inherent glowing qualities of the fluoro colours being brought to life when the entire sponge 10 is blood-soaked, which is significant as it renders an otherwise invisible sponge soaked in red blood visible to the naked eye during an operation.

Aside from the above, the fluoro-lime colour of the contrasting threads 22 in this embodiment is relatively soft yet eye-catching against the white background of the gauze 22 and hence readily visible in broad daylight. This offers the benefit of enabling the contrasting threads 22 to be very noticeable which is important during the quality control process in which any loose threads or debris are to be spotted and identified for removal. Also, it will be appreciated that the soft fluoro-coloured contrasting threads 22, without being too glaring or striking, serve the purpose of being a trade mark rendering the manufacturer, supplier or trader of the sponge 10A immediately identifiable to the user in a subtle fashion.

It should be noted that although not shown in the accompanying drawings, the threads 22 are made of one or more non-absorbing materials having a different texture from that of the gauze. These non-absorbing materials have different compositions and structures thereby giving rise to a contrasting texture and appearance. The threads 22 are not susceptible to being stained by blood or other fluids thereby being capable of maintaining their inherent appearance and visibility when in use. This is advantageous, particularly during surgery where sponges are usually soaked in red blood and hence easily confused with an organ. The non-absorbing threads with a contrasting appearance would reduce or eliminate the likelihood of any visual confusion.

Figure 3:
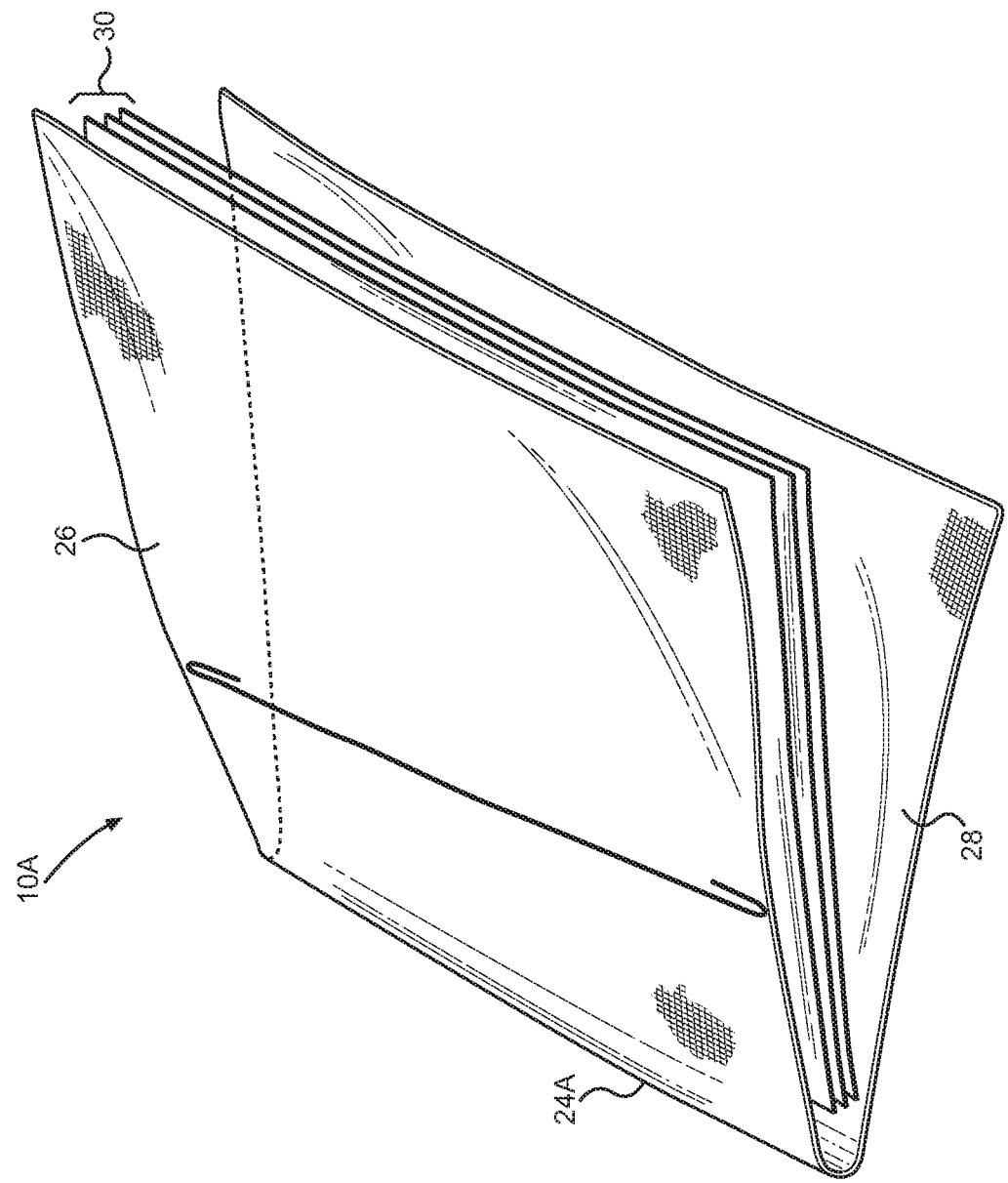
FIG. 3 is a partially exploded view of the sponge of FIG. 1.
Figure 4:
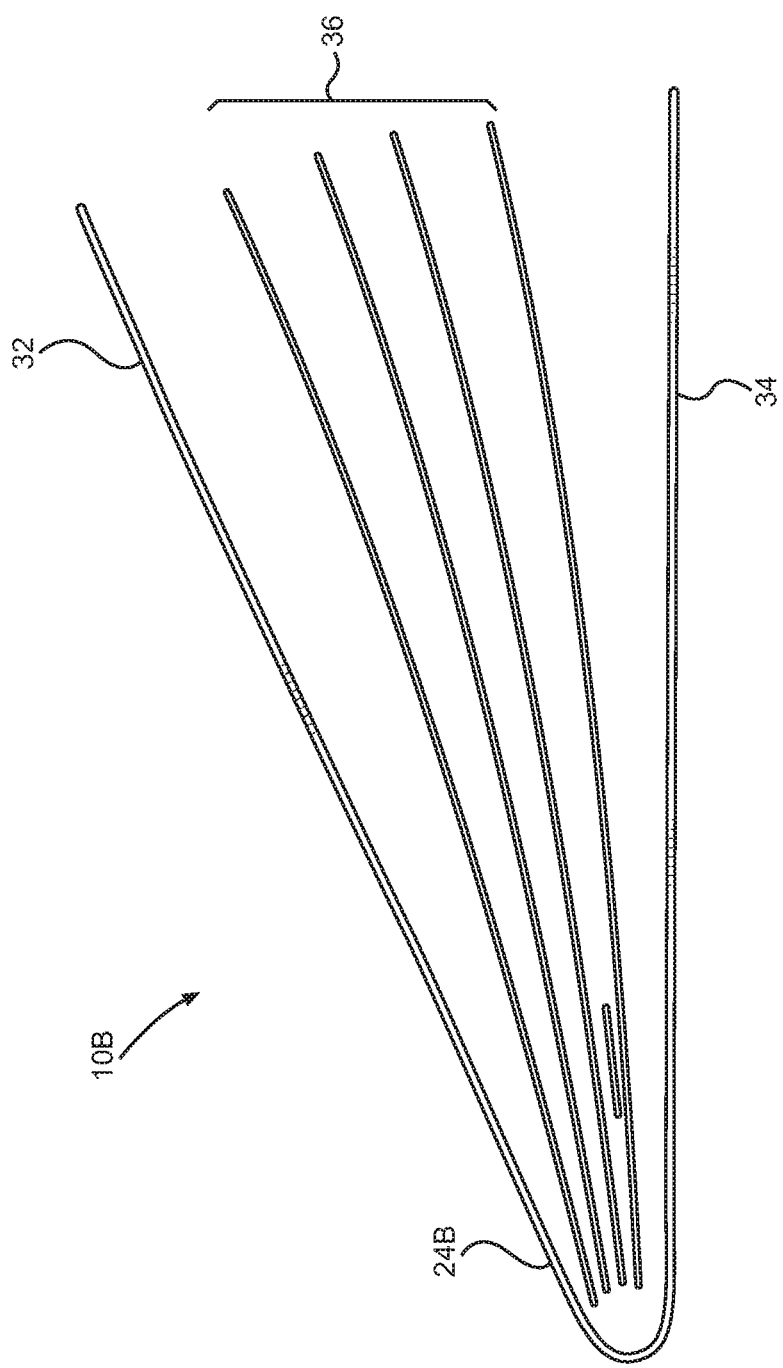
FIG. 4 is a partially exploded view of a 6-ply sponge in accordance with another preferred embodiment of the present invention.

Referring now to FIG. 3, a five-ply sponge 10A is shown. The five-ply sponge 10A has a continuous sheet 24A of cotton gauze folded in half to form top and bottom plies 26 & 28 and three intermediate plies 30 made out of non-woven viscose and/or polyester. The sponge 10A is capable of absorbing fluids up to 12 times its own weight thereby being perfect for oozing or weeping wounds.

Another embodiment of the sponge 10B is shown with six plies. The six-ply sponge 10B is partially formed by a continuous sheet 24B folded in half to form top and bottom plies 32 & 34. The sponge 10B also includes four intermediate plies 36 which are all made of cotton. The sponge 10B is capable of absorbing fluids up to 8 times its own weight.

Figure 5:
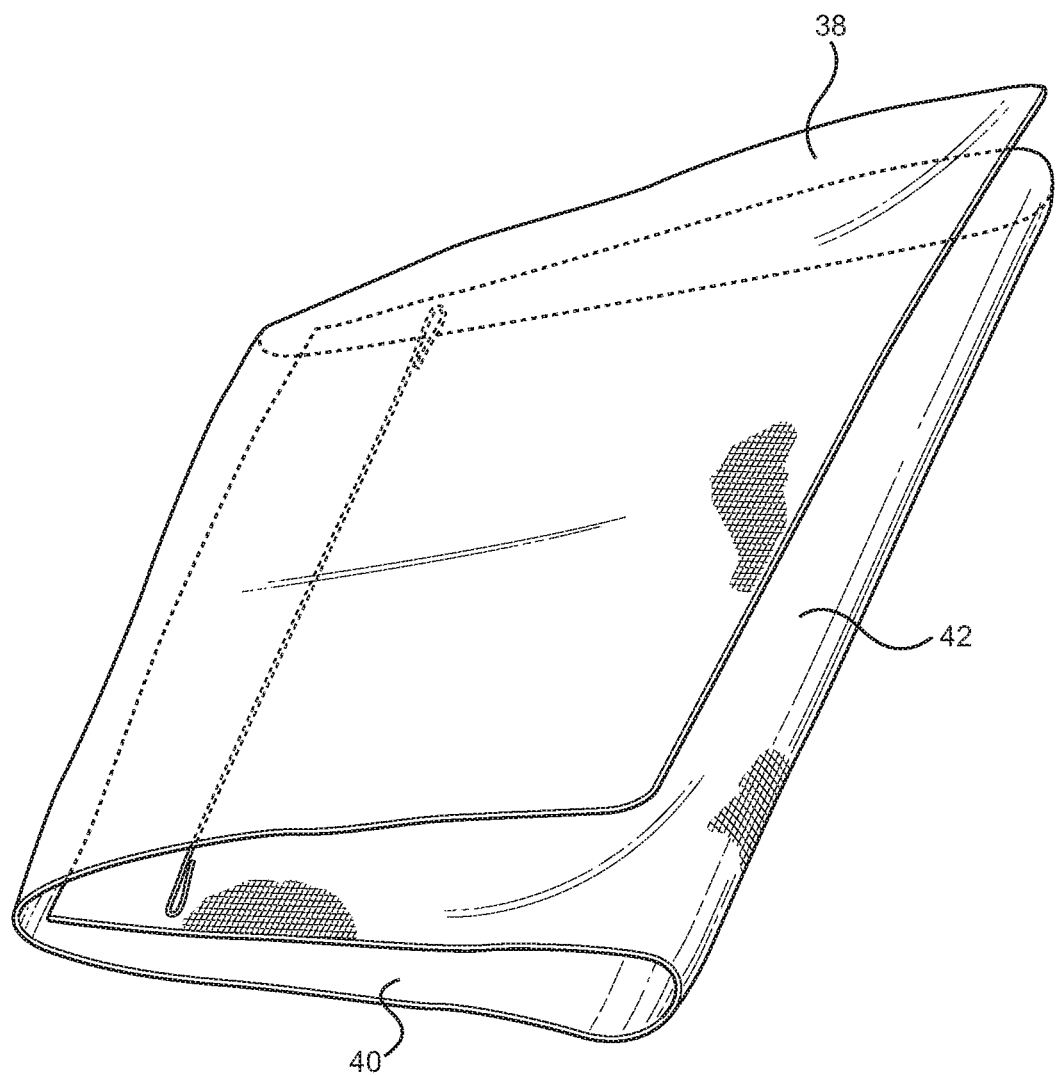
FIG. 5 is a schematic view of the cover layer of the sponge of FIG. 1 illustrating how it can be arranged.
Figure 6:
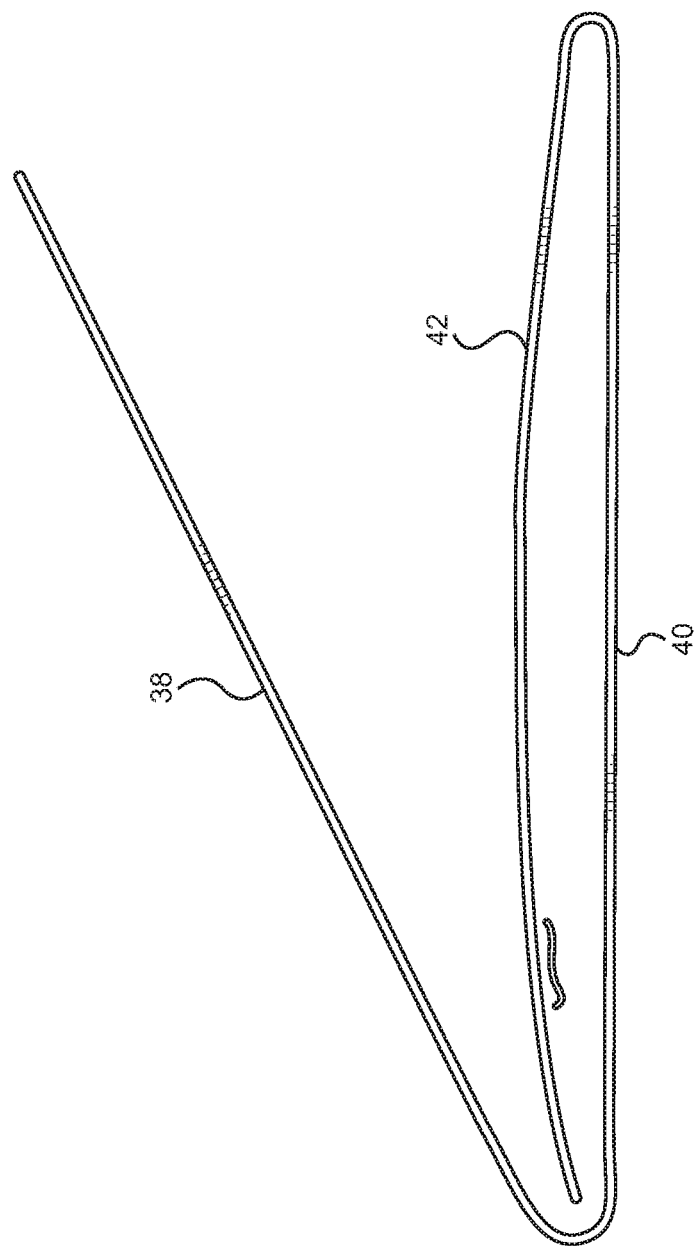
FIG. 6 is a side view of the sponge of FIG. 5.

As shown in FIGS. 5 and 6, the 'cover gauze 24A or 24B' may be arranged such that it is divided into three equal portions which are folded onto one another. As such, the intermediate plies 30 or 36 may be placed in between the folds. It should be noted that the number of intermediate plies may vary depending on the required application of the sponge.

Figure 7:
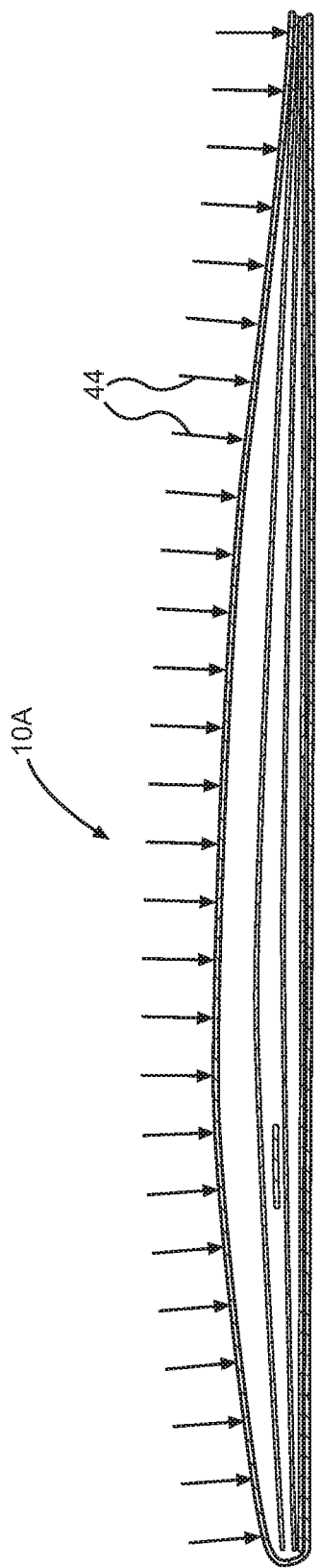
FIG. 7 is a cross-sectional view of the sponge of FIG. 3.
Figure 8:
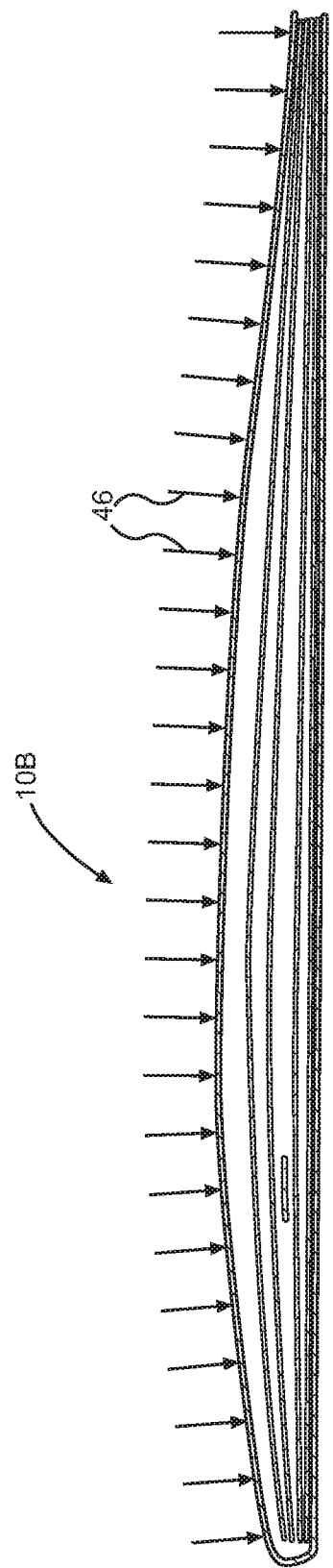
FIG. 8 is a cross-sectional view of the sponge of FIG. 4.

Referring to FIGS. 1 and 2, the sponge 10A or 10B of the present invention is substantially square in shape. Accordingly, the plies 30, for example, are also substantially square in shape. As shown in FIGS. 1 and 2, all of the plies of the sponge 10A, for example, are sewn together by contrasting threads 22 creating stitches 20 along and around the open sides 14, 16 & 18 as well as diagonally across the sponge 10A. As such, the diagonal stitches 20 form a cross over the surface of the sponge 10A. The location of the stitches 20 are best shown in FIGS. 7 and 8 by the downwardly pointing arrows 44 & 46. It will be appreciated that the sponge 10A or 10B may be rectangular in other embodiments. It should also be noted that the plies of the sponge have no exposed raw edges or those that have cut edges folded in so as to prevent unravelling or fraying.

As shown in FIGS. 1 to 8, the sponge 10A or 10B has an X-ray detectable thread 48 which may be a monofilament thread, multifilament yarn, a continuous strip or a similar insertion made out of a polyester thread and barium sulphate, for example, which is meant to be radiopaque to X-rays. This would enable the sponge 10A or 10B to be detectable via X-ray which is helpful when the sponge 10A or 10B is accidentally left inside a patient's body or wound.

Figure 9:
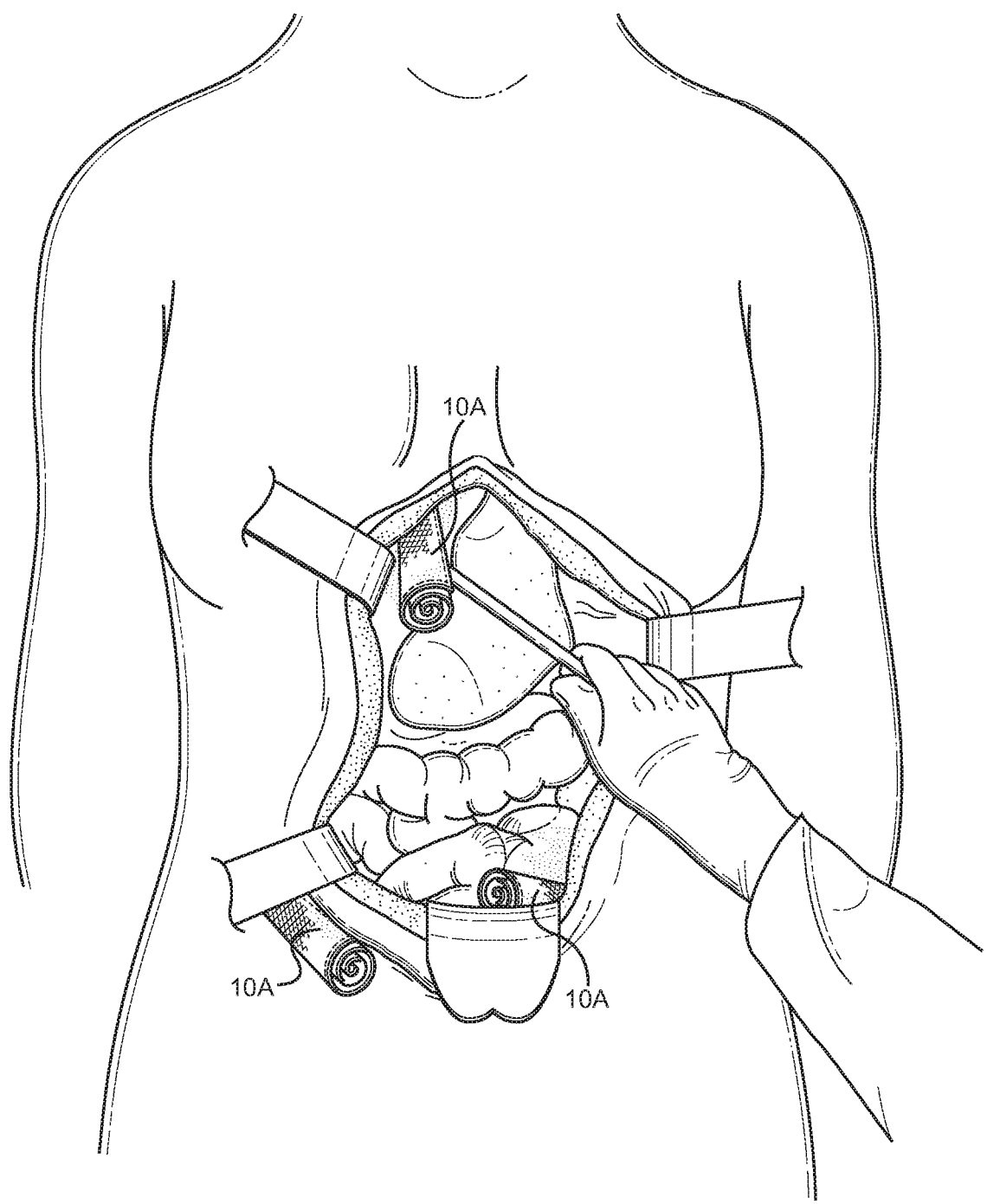
FIG. 9 is a front view of an open wound in a human body to which sponges of FIG. 1 are applied.

Referring to FIG. 9, three sponges 10A being in a folded and rolled-up form are used during an operation.

Now that a preferred embodiment of the present invention has been described in some detail, it will be apparent to a skilled person in the art that the surgical sponge of the present invention may offer at least the following advantages:

1. it improves the visibility and hence noticeability of the sponge when soaked in red being inside a cavity during an operation;
2. it functions as a trade mark rendering the manufacturer, supplier or trader of the sponge immediately recognisable to the user before, during and after use; and
3. it enables easy spotting of any loose threads or debris during the quality control process thereby reducing the likelihood of users having to return an item after opening the packaging and finding that the item is flawed.

Those skilled in the art will appreciate that the invention described herein is susceptible to variations and modifications other than those specifically described. For instance, when the colour of the gauze is not white but something different, the colour of the contrasting threads may vary so as to generate the contrasting effect. All such variations and modifications are to be considered within the scope and spirit of the present invention the nature of which is to be determined from the foregoing description.

The invention claimed is:

1. A surgical sponge comprising:
   multiple plies of gauze having one or more open sides; and
   stitches made with one or more contrasting threads and adapted to fasten or close the open sides;
   wherein the contrasting threads are made of one or more non-absorbing materials, the non-absorbing materials of the contrasting threads having a soft or subdued fluoro colour that is a combination of at least fluoro-green and fluoro-yellow.

2. The surgical sponge of claim 1, wherein the threads are in contrast to the gauze by the fluoro colour and by physical texture.

3. The surgical sponge of claim 1, wherein the gauze is white in colour.

4. The surgical sponge of claim 1, which is five-ply or six-ply.

5. The surgical sponge of claim 4, which, in the case of being five-ply, includes a sheet of cotton gauze folded in half to form top and bottom plies and three intermediate plies made out of non-woven viscose and/or polyester.

6. The surgical sponge of claim 4, which, in the case of being six-ply, includes six plies of cotton gauze.

7. The surgical sponge of claim 4, which is partially formed by a sheet of cotton gauze being divided into three equal portions which are folded onto one another.

8. The surgical sponge of claim 4, wherein each ply is rectangular or square in shape.

9. The surgical sponge of claim 4, wherein the plies of the sponge are sewn together by the one or more threads creating stitches along and around the open sides.

10. The surgical sponge of claim 9, wherein further stitches are provided diagonally across the surface of the sponge.

11. The surgical sponge of claim 1, wherein:
- each of the multiple plies is rectangular or square in shape; and
- the multiple plies of the sponge are sewn together by the one or more threads creating stitches along and around three sides of each of the multiple plies.

12. The surgical sponge of claim 11, wherein a fourth side of each ply is stitch-free.

\* \* \* \* \*